United States Patent
Mayor Sans et al.

(10) Patent No.: US 9,248,211 B2
(45) Date of Patent: Feb. 2, 2016

(54) SYSTEM FOR DELIVERING VOLATILE SUBSTANCES

(71) Applicant: Zobele Espana, S.A., Barcelona (ES)

(72) Inventors: Fernando Mayor Sans, Barcelona (ES); Elisabeth Martinez de Morentin Pujabet, Barcelona (ES); Joaquim Llorente Alonso, Barcelona (ES)

(73) Assignee: ZOBELE ESPAÑA, S.A., Barcelona (ES)

( * ) Notice: Subject to any disclaimer, the term of this patent is extended or adjusted under 35 U.S.C. 154(b) by 132 days.

(21) Appl. No.: 14/071,052

(22) Filed: Nov. 4, 2013

(65) Prior Publication Data
US 2014/0124964 A1 May 8, 2014

(30) Foreign Application Priority Data

Nov. 6, 2012 (EP) .................................. 12382430

(51) Int. Cl.
*B01F 3/04* (2006.01)
*A61L 9/12* (2006.01)
*A01M 1/20* (2006.01)

(52) U.S. Cl.
CPC .............. *A61L 9/122* (2013.01); *A01M 1/2033* (2013.01); *B01F 3/04* (2013.01); *A61L 2209/133* (2013.01); *A61L 2209/134* (2013.01)

(58) Field of Classification Search
CPC ......... B01F 3/04; A61L 9/122; A01M 1/2033
USPC ............................................ 261/30, DIG. 88
See application file for complete search history.

(56) References Cited

U.S. PATENT DOCUMENTS

| | | | |
|---|---|---|---|
| 2,765,194 A * | 10/1956 | Will | 239/59 |
| 4,621,768 A | 11/1986 | Lhoste et al. | |
| 4,995,555 A | 2/1991 | Woodruff | |
| 5,772,074 A * | 6/1998 | Dial et al. | 222/1 |
| 6,966,500 B1 | 11/2005 | Kelley | |
| 7,243,859 B2 | 7/2007 | Caserta et al. | |
| 8,485,454 B1 | 7/2013 | Irvin et al. | |

FOREIGN PATENT DOCUMENTS

| | | |
|---|---|---|
| EP | 0 070 173 A1 | 1/1983 |
| WO | 2007110086 A1 | 4/2007 |
| WO | 2011140917 A1 | 11/2011 |

OTHER PUBLICATIONS

Extended European Search Report from European Patent Application 13191375.8, Jan. 22, 2014, 6 pp., mailed from European Patent Office, Munich, Germany.
Non-Final Office action from U.S. Appl. No. 14/071,176, filed Nov. 4, 2013, 12 pgs., mailed from the United States Patent and Trademark office on Jul. 31, 2015.

* cited by examiner

*Primary Examiner* — Robert A Hopkins
(74) *Attorney, Agent, or Firm* — Baker & Hostetler LLP

(57) ABSTRACT

The system for delivering volatile substances (1) comprises a container (2) inside of which a volatile substance is housed; a ventilation surface (3) placed in said container (2) provided with ventilation windows; and a fan (4) for creating the ventilation of the fragrance of said volatile substance; and is characterized in that said fan (4) is placed over said ventilation surface (3), suctioning the fragrance of said volatile substance.
It permits to optimize the evaporation of the fragrance of the volatile substance, expending the least energy possible.

5 Claims, 1 Drawing Sheet

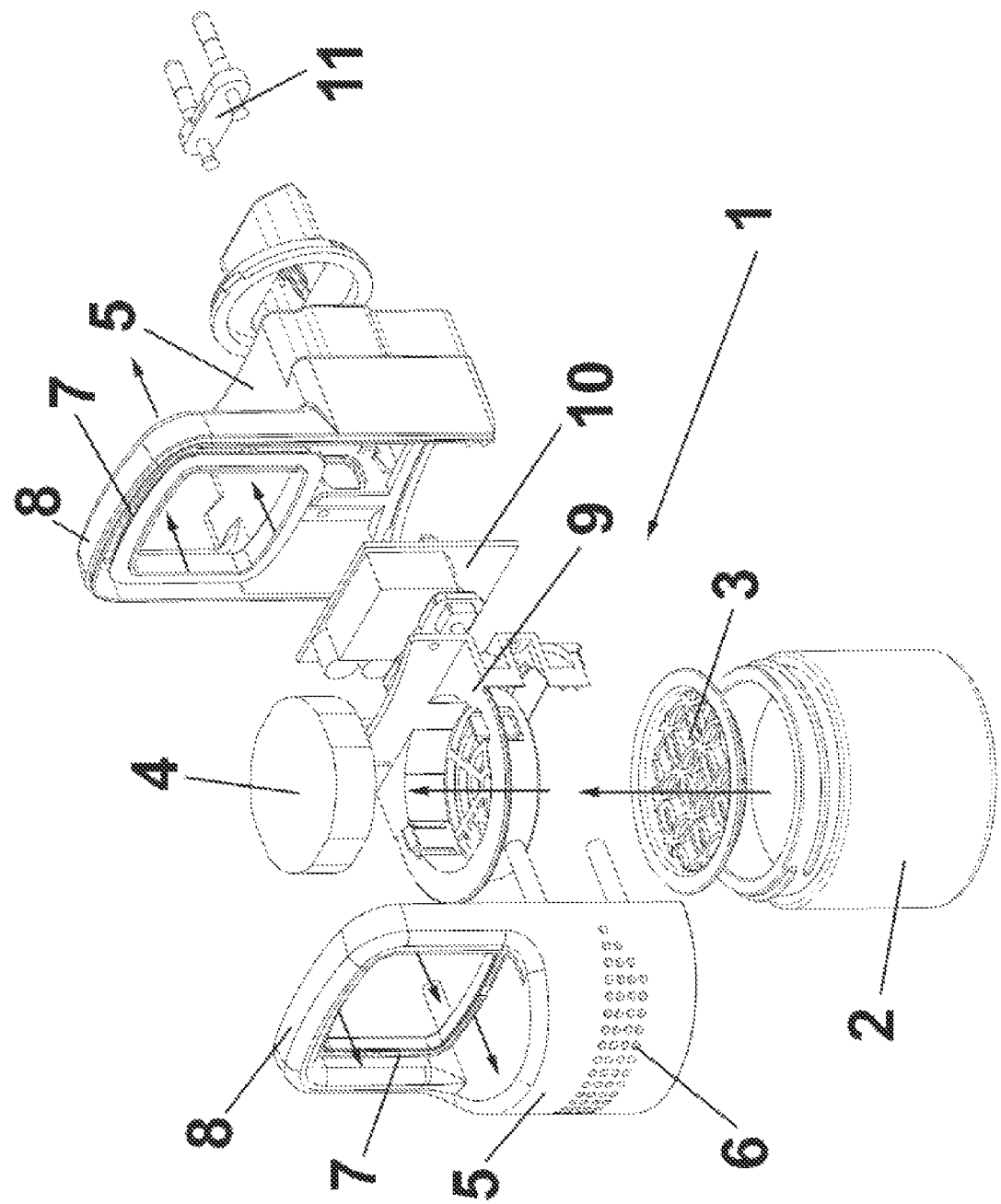

SYSTEM FOR DELIVERING VOLATILE SUBSTANCES

The present refers to a system for delivering volatile substances that comprises a fan for generating an airflow with a fragrance generated by a volatile substance. The present application claims the benefit of European Patent Application Serial No. 12382430.2, with a filing date of Nov. 6, 2012.

BACKGROUND OF THE INVENTION

A type of air fresheners or systems for delivering volatile substances currently known in the art is comprised of a container or receptacle inside of which an air freshening substance or volatile substance is housed.

During the manufacturing of said container it is hermetically sealed so that the air freshener product conserves its full fragrance, in such a way that when wanting to use it the sealing or hermetic seal must be removed.

A problem with these air fresheners or systems for delivering volatile substances currently known in the art is that simply opening a recipient or container does not produce a desired dispersion of the fragrance of said air freshener product.

For solving this drawback, there are already systems known in the art for delivering volatile substances that comprise a fan for generating an airflow for the correct dispersion of the fragrance of said air freshener product.

Although obviously the fan generates a stronger airflow than in systems for delivering volatile substances without a fan, the lateral placement of the fan for provoking the impulse of fragrance does not optimize its evaporation.

Therefore, one purpose of the present invention is to provide a system for delivering volatile substances in which the evaporation of the fragrance of a volatile substance is optimized, expending as little energy as possible.

DESCRIPTION OF THE INVENTION

With the system for delivering volatile substances of the invention it is possible to solve the cited drawbacks, providing other advantages that are described below.

The system for delivering volatile substances of the present invention comprises:

a container inside of which a volatile substance is housed;

a ventilation surface placed in said container provided with ventilation windows; and a fan for the ventilation of the fragrance of said volatile substance, and that is characterized in that said fan is placed over said ventilation surface, promoting the suction of the fragrance of said volatile substance.

Advantageously, said fan is placed in a substantially parallel position with respect of said ventilation surface, that is, in a horizontal position in accordance with the position of use of the system for delivering volatile substances.

Preferably, said container is housed inside a carcass provided with an air intake and an outlet for the air suctioned by said fan.

In accordance with a preferred embodiment, said air outlet is formed by a groove through which the air suctioned by the fan passes, said groove preferably being placed in a frame that protrudes from said container.

In accordance with a preferred embodiment, the air intake is made of a plurality of holes.

Advantageously, said fan is associated to an on/off and or regulating push button and/or fan operating regulator. Furthermore, said fan is fed by a battery or electric grid.

By positioning the fan over the ventilation surface a more efficient evaporation is obtained, given that it does not blow over the volatile substance, but rather it suctions the fragrance of said volatile substance.

BRIEF DESCRIPTION OF THE DRAWINGS

For a better understanding the above explanation and for the sole purpose of providing an example, some non-limiting drawings are included that schematically depict a practical embodiment.

FIG. 1 is an exploded perspective view of the system for delivering volatile substances of the present invention.

DESCRIPTION OF A PREFERRED EMBODIMENT

FIG. 1 depicts an exploded view of the components comprising the system for delivering volatile substances of the present invention, identified overall by reference number 1.

Said system for delivering volatile substances 1 comprises a container 2 inside of which a volatile substance or air freshener product that provides a fragrance (not represented) is housed. Said container 2 includes an opening above which a ventilation surface 3 is placed, provided with a plurality of windows, through which the fragrance of said volatile substances passes. Said ventilation surface 3 is, for example, a screen, which also prevents accidental contact with the volatile substance.

Preferably, said ventilation surface 3 is mounted in a fixed manner over said opening of container 2, such that it can be removed when it is necessary to refill the container 2 with a new volatile substance.

To increase the evaporation of the fragrance of the volatile substance, the system for delivering volatile substances 1 comprises a fan 4 that is placed over said ventilation surface 3, in such a way that said fragrance will be suctioned towards outwardly from the container 2.

As can be seen in FIG. 1, said fan 4 is placed substantially parallel to said ventilation surface 3, that is, in a position substantially horizontal in the normal use position of the system for delivering volatile substances, just as shown in the figures. This positioning of the fan 4 provides a more efficient evaporation of the fragrance of the volatile substance.

Between the fan 4 and the ventilation surface 3, preferably an intermediate piece 9 is placed as a support means, which comprises a housing for the fan 4, also provided with a plurality of windows to allow the passage of air.

The system for delivering volatile substances 1 of the present invention also comprises a carcass 5, formed by two halves as can be seen in FIG. 1. Inside said carcass 5 the container 2, the ventilation surface 3, the intermediate piece 9 and the fan 4 are housed, in such a way that the interior of the carcass 5 remains sealed, except for an air intake 6 and an air outlet 7.

Said air intake 6 into the carcass 5 is preferentially made up of a plurality of holes located on a side of the carcass 5, while air outlet 7 is preferably formed by a groove located on a frame 8 that protrudes from said carcass 5.

Said frame 8 has a substantially square profile, although it could have any suitable profile and, in this way, the user does not have access to the fan 4; the fragranced air exiting through this groove of the air outlet 7.

The device of the present invention also comprises a printed circuit board 10 for controlling the operation of the fan 4. To this end, in the carcass 5 an on/off push button (not depicted) will be placed, or any other type of control that enables controlling the rotation speed of the fan 4 or that fan 4 operates in an intermittent manner, for example to optimize energy consumption.

Said fan 4 can be fed by one or various batteries or can be connected to the electric grid, for example with a plug 11.

In order to facilitate the operating compression of the system for delivering volatile substances 1 of the present invention, in FIG. 1 the airflow has been indicated by means of some arrows. In this way, the fan 4 causes a suction of the air inside container 2 coming from said air input holes 6. The air passes through the ventilation surface 3, the housing of the fan 4 of the intermediate piece 9, and exists through said groove of the air outlet 7, freshening the air around the system for delivering volatile substances 1.

Even though reference has been made to a specific embodiment of the invention, it is obvious to a person skilled in the art that the system for delivering volatile substances described herein is susceptible to numerous variations and modifications, and that all of the details mentioned can be substituted for other technically equivalent ones without departing from the scope of protection defined by the attached claims.

What is claimed is:

1. System for delivering volatile substances (1), that comprises:

- a container (2) inside of which a volatile substance is housed;
- a carcass (5) housing said container where said carcass is provided with an air intake (6) and with an air outlet (7);
- a ventilation surface (3) placed in said container (2) provided with ventilation windows; and
- a fan (4) for the ventilation of a fragrance of said volatile substance,
- said fan (4) being placed over said ventilation surface (3) suctioning the fragrance of said volatile substance, characterized in that said air outlet is formed by one groove (7) through which passes the fragrance drawn by said fan (4), said groove (7) being placed in a frame (8) that protrudes from said carcass (5).

2. System for delivering volatile substances (1) according to claim 1, characterized in that said fan (4) is placed in a substantially parallel position with respect to said ventilation surface.

3. System for delivering volatile substances (1) according to claim 1, characterized in that said air intake is made up of a plurality of holes (6).

4. System for delivering volatile substances (1) according to claim 1, characterized in that said fan (4) is associated with an on/off and/or fan operating regulator push button.

5. System for delivering volatile substances (1) according to claim 1, characterized in that said fan (4) is fed with a battery or an electric network.

* * * * *